United States Patent
Gordon

(10) Patent No.: US 7,844,471 B2
(45) Date of Patent: Nov. 30, 2010

(54) SYSTEM AND METHOD FOR ASSESSMENT AND CORRECTIVE ACTION BASED ON GUIDELINES

(75) Inventor: Tim H. Gordon, River Vale, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/806,749

(22) Filed: Jun. 4, 2007

(65) Prior Publication Data

US 2007/0239486 A1 Oct. 11, 2007

Related U.S. Application Data

(63) Continuation of application No. 10/153,883, filed on May 24, 2002.

(51) Int. Cl.
*G06Q 10/00* (2006.01)
*G06Q 50/00* (2006.01)

(52) U.S. Cl. .................... 705/2; 705/3; 434/262

(58) Field of Classification Search ............. 705/2, 705/3; 345/473; 434/262; 463/42; 604/67; 706/46; 715/716
See application file for complete search history.

(56) References Cited

U.S. PATENT DOCUMENTS

| | | | |
|---|---|---|---|
| 5,279,294 A | 1/1994 | Anderson et al. | |
| 5,536,249 A | 7/1996 | Castellano et al. | |
| 5,583,758 A | 12/1996 | McIlroy et al. | |
| 5,953,704 A | 9/1999 | McIlroy et al. | |
| 6,192,891 B1 | 2/2001 | Gravel et al. | |
| 6,230,142 B1 | 5/2001 | Benigno et al. | |
| 6,280,409 B1 * | 8/2001 | Stone et al. | 604/67 |
| 7,391,420 B1 * | 6/2008 | Coyne | 345/473 |
| 2002/0072933 A1 | 6/2002 | Vonk et al. | |
| 2002/0107824 A1 * | 8/2002 | Ahmed | 706/46 |

OTHER PUBLICATIONS

Mazze et al., Staged Diabetes Management, A Systematic Approach; International Diabetes Center; Minneapolis, MN, 2000; Title page-p. 20.

* cited by examiner

*Primary Examiner*—Linh Michelle Le
(74) *Attorney, Agent, or Firm*—Roylance, Abrams, Berdo & Goodman, L.L.P.

(57) ABSTRACT

A system and method are provided for applying guidelines to data and providing self-assessment ability. Guideline data is stored in a data storage component, along with user data. The user data represents both quantitative data and qualitative self-assessment data. In a self-assessment system and method, a graphical user interface is provided along with a target image and factor icons. The icons are adapted to be moved onto a position on the target image representative of an entity's self assessment of performance relative to the corresponding factor. A subset of actionable alternatives are selected and displayed based on the self-assessment data and the guidelines.

11 Claims, 15 Drawing Sheets

INTRODUCTION:
Welcome to your diabetes Control Assistant™.

Patients using the BD Trinity™ diabetes control system together with this Control Assistant software have <u>improved</u> <u>their diabetes control by xx%</u>.

Control Assistant works because it is <u>based on Staged</u> <u>Diabetes Management™</u>, a leading diabetes therapy guidance system that doctors use to get better results for their diabetes patients worldwide.

FIG. 5

INTRODUCTION:
Together Trinity and Control Assistant work like this:

1. You and your doctor program your therapy regimen and diabetes control targets into your Trinity device.

2. Trinity uses your glucose and insulin dose values to determine progress reaching target.

3. Trinity confirms your progress with a green signal, or alerts you to a possible problem with a red or yellow signal.

4. When you receive a yellow or red signal, Control Assistant helps tell you why and what you can do about it.

FIG. 6

Control Assistant™ Set-up:
Name: Donna Donner
Current regimen: 2 injections per day - SDM stage 2 
Glucose Control Data:
SMBG Target Range: 80 - 140 mg/dl 
Target rate of SMBG improvement: SDM default: 15 - 30 mg/dl per month 
Maximum insulin dose: SDM default: 1.5 units/kg. 
Standards of Care Data:
Most recent HbA1c 8.3 on May 14, 2001 
Last foot exam: Sensate on May 14, 2001 
etc.
FIG. 7

INTRODUCTION:
Congratulations, you have successfully set-up your Control Assistant.

Now, each glucose test you perform will be <u>compared against your targets.</u>

As long as your diabetes control is <u>on target,</u> Trinity will give you a <u>green signal.</u>

If you get a <u>red or yellow signal,</u> re-connect your Trinity to Control Assistant to <u>find out why and what to do.</u>

FIG. 8

Your assessment indicates that for you, maintaining your food plan may be the most difficult part of diabetes control.

Food plan adherence is very difficult for many people with diabetes, but there are things that you can do about it.

Have you had nutrition education from a,

Dietician? Yes No
Nurse or other medical professional? Yes No

Do you have a daily plan for calories and carbohydrates? Yes No

Do you keep a record of what you eat each day? Yes No

Do you keep a record of what you eat each day? Yes No

FIG. 14

> Your assessment indicates that for you, maintaining your food plan may be the most difficult part of diabetes control.

Food plan adherence is very difficult for many people with diabetes, but there are things that you can do about it.

Have you had nutrition education from a,

Dietician? Yes ☐ No ☑
Nurse or other medical professional? Yes ☑ No ☐

Do you have a daily plan for calories and carbohydrates? Yes ☑ No ☐

Do you keep a record of what you eat each day? Yes ☐ No ☑

Do you keep a record of what you eat each day? Yes ☐ No ☑

FIG. 15

SYSTEM AND METHOD FOR ASSESSMENT AND CORRECTIVE ACTION BASED ON GUIDELINES

This application is a continuation of U.S. patent application Ser. No. 10/153,883, filed May 24, 2002, the entire content of which is hereby incorporated by reference.

FIELD OF THE INVENTION

In general, the invention relates to a system and method for assisting an entity to reach a goal within a set of guidelines, including incorporating self-assessment of performance data into suggestions for corrective action. More particularly, the invention relates to a diagnostic and medication delivery system for monitoring and recording property levels in a patient as well as medication doses received by the patient, for alerting the patient if monitored levels fall outside a clinical target range, and for assisting a patient with determining corrective action to return the patient to prescribed property levels according to a clinical plan.

BACKGROUND OF THE INVENTION

As the population in the United States continues to increase, especially among the aging, the ability for traditional healthcare providers, such as hospitals and doctors' offices, to effectively provide treatment becomes increasingly challenging. In addition, as the average age of the population continues to increase, the number of people requiring care for long-term illnesses, such heart disease, diabetes and the like also increases.

Accordingly, alternatives to traditional health providers are being developed to accommodate these greater healthcare needs. Also, more effective and efficient systems are being developed to attempt to reduce the number of medical personnel necessary to treat or monitor patients. Specifically, systems are being developed that enable patients to have their conditions monitored at home, such as by themselves or a visiting nurse, and to provide data related to various tests, such as blood pressure measurement, temperature, weight, blood glucose level, and the like, to a centralized database. These systems are then capable of organizing the data in an appropriate manner, and providing the data in an appropriate format to a healthcare provider, such a physician, who can review the data and determine whether the plan of care for the patient is sufficient or should be modified.

An example of a healthcare data manipulation and analysis system is described in U.S. Pat. No. 6,230,142 to Benigno, the entire content of which is incorporated herein by reference. According to the disclosure of the Benigno patent, a healthcare provider, such as a nurse, can obtain patient data during a visit with the patient at, for example, the patient's home. This patient data is entered into a database that compares the data to treatment guidelines for the particular patient's disease, and provides a recommended course of treatment for the patient. Other examples of this type of system are described in U.S. Pat. Nos. 5,953,704 and 5,583,758, both to McGilroy, the entire content of both of these patents being incorporated herein by reference.

Although the patents cited above describe systems which attempt to gather and analyze patient data and provide some recommended plan of treatment, these systems are not configured to outline different options of patient care. These systems also are not effective in illustrating to the care provider a comparison between other variations of care plans that could be followed based on variations in the patient data. Therefore, healthcare providers may find these types of systems insufficient because they provide only a specific result for the patient based on the specific patient test data, and not different options that could be provided to the patient were the test data to be different.

A system known as Staged Diabetes Management (SDM) has been developed to assist medical practitioners in managing a patient's disease by comparing patient data with a set of guidelines for treatment options. SDM is described in further detail in Mazze et al., Staged Diabetes Management, A systematic Approach; International Diabetes Center; Minneapolis, Minn., 2000, which is incorporated herein in its entirety.

Although the SDM technique has been very successful, it is somewhat difficult to implement in a practical sense because of the need to manually integrate patient data with the SDM guidelines. That is, when a healthcare provider uses the known SDM technique, the healthcare provider must manually compare the patient data, such as test measurements and the like, with the questions and criteria set forth in the decision paths. Based on this comparison, the healthcare provider manually determines the course of treatment to provide to the patient in view of the guidelines outlined in the decision path. Again, although this technique is successful in achieving the desired results, it may be somewhat difficult for a healthcare provider to use in a practical sense.

An improvement of the SDM concept is described in copending U.S. Patent Application of Tim H. Gordon et al., filed Nov. 1, 2001, entitled "System and Method for Integrating Data with Guidelines to Generate Displays Containing the Guidelines and Data," the contents of which are expressly incorporated herein in their entirety. However, this improved system and method are still primarily intended for use by a health care professional, rather than a patient.

Home diabetes therapy requires the patient to carry out a prescribed regimen that involves self-testing blood glucose levels and administering an appropriate dose of insulin. Insulin has traditionally been injected by a hypodermic syringe, which suffers from numerous drawbacks. For example, syringes are not preloaded with medication, requiring the user to carry a separate medical vial. Syringes also require a degree of dexterity and sufficient visual acuity on the part of the patient to line up the needle of the syringe with the rubber septum on the medical vial and to ensure that the syringe is loaded with the proper dosage. As a result, unintentional needle pricks can occur.

To overcome the drawbacks of syringes, medication delivery pens have been developed, which facilitate the self-administration of medication such as insulin. Such delivery pens use prepackaged insulin and may be used repeatedly until the medication is exhausted. Mechanical and electronic pens are available to the patient. Electronic pens incorporate electronic circuitry that sets and/or indicates the appropriate dosage of insulin and stores data for subsequent downloading such as the time, date, amount of medication injected, and so on.

Glucose levels are monitored at periodic intervals to determine when another insulin injection should be taken or to determine how the user is responding to prior injections. The patient monitors blood levels by lancing a portion of the body with a lancet to take a blood sample. The blood sample is placed on a test strip that contains appropriate reagents for creating the chemical reactions necessary to measure glucose levels, which is subsequently analyzed by the blood glucose monitor. Typically, the patient then manually records the results, the time and date in a log book. To monitor glucose levels the patient is required to have available a lancet, test strips and a blood glucose monitor.

The self-treatment of diabetes therefore requires the patient to carry at least three devices: a medication delivery pen, a blood glucose monitor, and a lancet, as well as ancillary items such as test strips, lancets and needles. This can be inconvenient, and cumbersome to use.

A number of patents disclose systems that attempt to allow a patient to more conveniently perform the requisite procedures for treating diabetes. More particularly, U.S. Pat. No. 5,279,294, to Anderson et al., discloses a portable unit that includes a glucose monitor and a lancet. The monitor and lancet are integrated in the housing. The lancet is not an independent component operably distinct from the housing. Rather, the housing includes a spring-actuated hammer for driving a disposable lancet. Since the lancet is integrated with the housing, it cannot be removed and used separately from the housing. U.S. Pat. No. 5,536,249, to Castellano et al., discloses a medication delivery pen that is integrated with a blood glucose monitor. The pen and monitor are not independent units and thus cannot be used separately from one another.

U.S. Pat. No. 6,192,891, to Gravel et al., which is expressly incorporated herein by reference in its entirety, discloses an integrated portable diagnostic and medication delivery system. The system includes a housing and a monitor disposed in the housing for monitoring a characteristic of a bodily fluid sample obtained from an individual. A medication delivery pen and a lancet are each removably mounted to the housing. The monitor, which may be integrated into the housing, may monitor blood glucose levels, for example, and the pen may be employed for the delivery of insulin.

While the above described systems facilitate the self-administration and monitoring of medication, there is a need for additional features and improvements for such systems. None of the known systems provide feedback to the patient in order to assist the patient in maintaining preset clinical values. While the Gravel device is capable of monitoring and recording dose and monitored substance levels in an electronic logbook, the device is a "measure only" device, and does not provide feedback to the patient other than displaying measured substance or dosage levels. Thus, where a patient is deviating from clinical targets, intervention is not possible until the various measurements recorded by the patient (and/or the device) are reviewed by a health care professional (HCP). Furthermore, because the device does not provide immediate feedback, the patient is unaware and therefore unable to take corrective action immediately.

Therefore there is a need for an improved medical therapy guidance system. Such a system would monitor a patient's progress based on recorded medication dose and property level measurements, and provide immediate feedback to inform the patient if they are on target, or if they are danger of deviating from their therapy target. Furthermore, it would be advantageous for a therapy guidance device to guide patients to perform self-assessments, and to inform patients of ways to take corrective actions in order to return to therapy targets. Finally, such a device would empower the patient to become a partner with their HCP in reaching a therapy goal.

SUMMARY OF THE INVENTION

The above described disadvantages are overcome, and other advantages are realized, in a system and method according to the present invention. The invention is embodied in a system for self-assessment and corrective action based on guidelines. The system includes a data storage component, for storing guideline data representing guidelines for assessing the condition of a person or guidelines for taking action on the person. The data storage component also stores user data representing both quantitative data, and qualitative self-assessment data. The system also includes an output device adapted to display a representation of at least a portion of the user data to at least a portion of the guideline data.

Another embodiment of the invention is a method of disease management. The method comprises storing guidelines data including guidelines for assessing the condition of a person and guidelines for taking action on the person in a memory. The method further comprises setting acceptable range and therapy plan values in a device which is adapted to measure a property in an entity, measuring the property, and storing measured property data representing the value of the property measured and the time the property was measured. The method includes comparing the measured property data to a subset of the guidelines data, and based on the comparison, alerting the user of the device if the measured property data values are not within an acceptable range, or are in danger of falling outside the acceptable range.

The invention is also embodied in a device of self-assessment of disease management. The device comprises a graphical user interface, and includes a target image and at least one factor icon. The factor icon is adapted to be moved to a position on the target image that is representative of the user's self-assessment of performance relative to the factor.

Still another embodiment of the invention is a method of self-assessment of disease management. The method comprises moving a factor icon in a graphical user interface including a target image to a position on the target image representative of a self-assessment of performance related to the factor, and based on the position, selecting a subset of suggestion data and displaying the suggestion data on a display.

Yet another embodiment of the present invention is a computer readable medium of instructions adapted to control a system for self-assessment of disease management. The computer readable medium of instructions includes a first set of instructions adapted to control a graphical user interface to display a target image and at least one factor icon. A second set of instructions is adapted to control the system to allow the user to move the at least one factor icon to a position on the target image representative of the user's self assessment of performance relative to the factor. A third set of instructions is adapted to select, based on the self-assessment, a subset of suggestions for performance improvement. Finally, a fourth set of instructions is adapted to display the subset of suggestions. The suggestions can include links to further instructional materials including audio-visual instructional presentations.

BRIEF DESCRIPTION OF THE DRAWINGS

The invention will be more readily understood with reference to the attached drawings figures, in which:

FIGS. 5-8 illustrate exemplary screen shots for setting target and therapy values in a disease management system according to an embodiment of the invention;

FIGS. 11-15 illustrate screen shots of a self-assessment system in accordance with an embodiment of the invention.

In the drawing figures, it will be understood that like numerals refer to like features and structures.

DETAILED DESCRIPTION OF THE PREFERRED EMBODIMENTS

Figure 1:
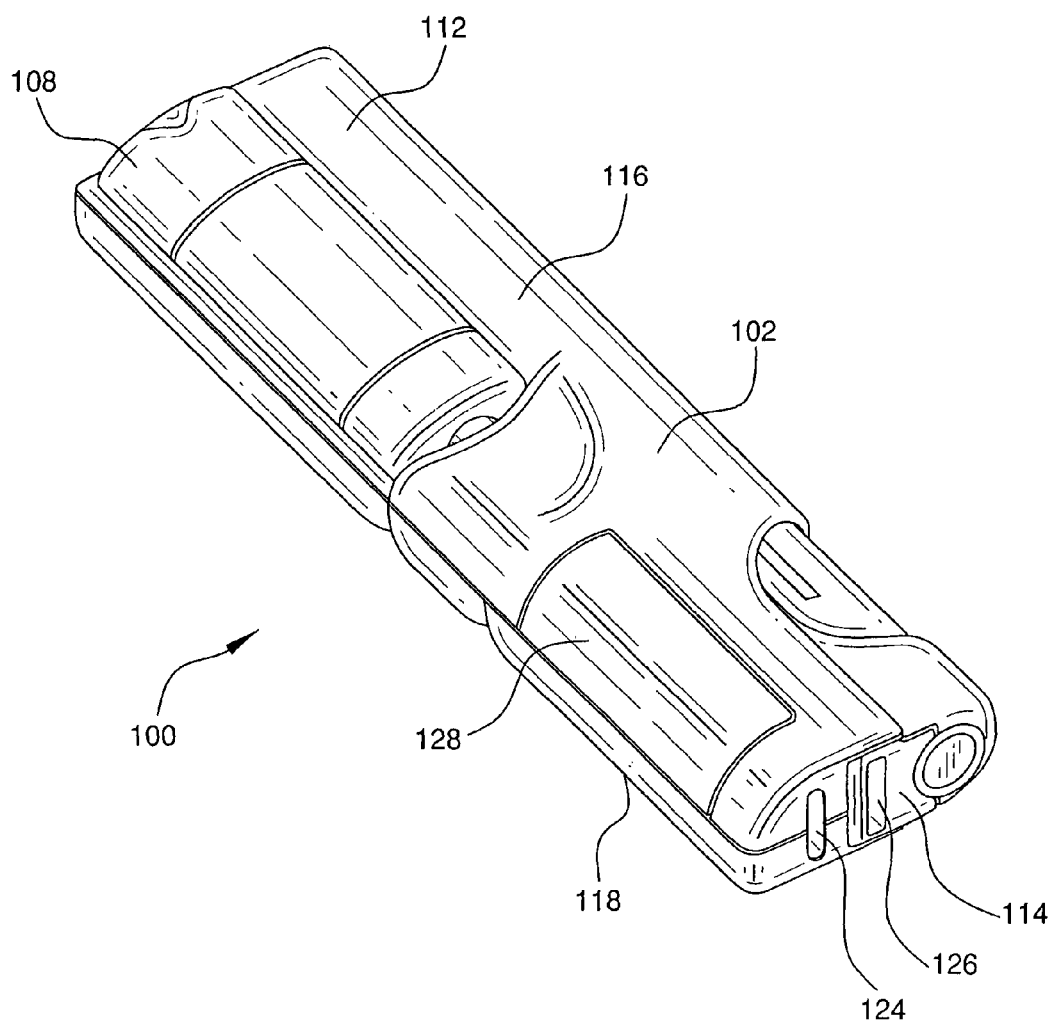
FIGS. 1-3 illustrate a device for medication delivery, measurement of a property, and storage of dosage and property data for integration with a disease management system in accordance with an embodiment of the present invention.
Figure 2:
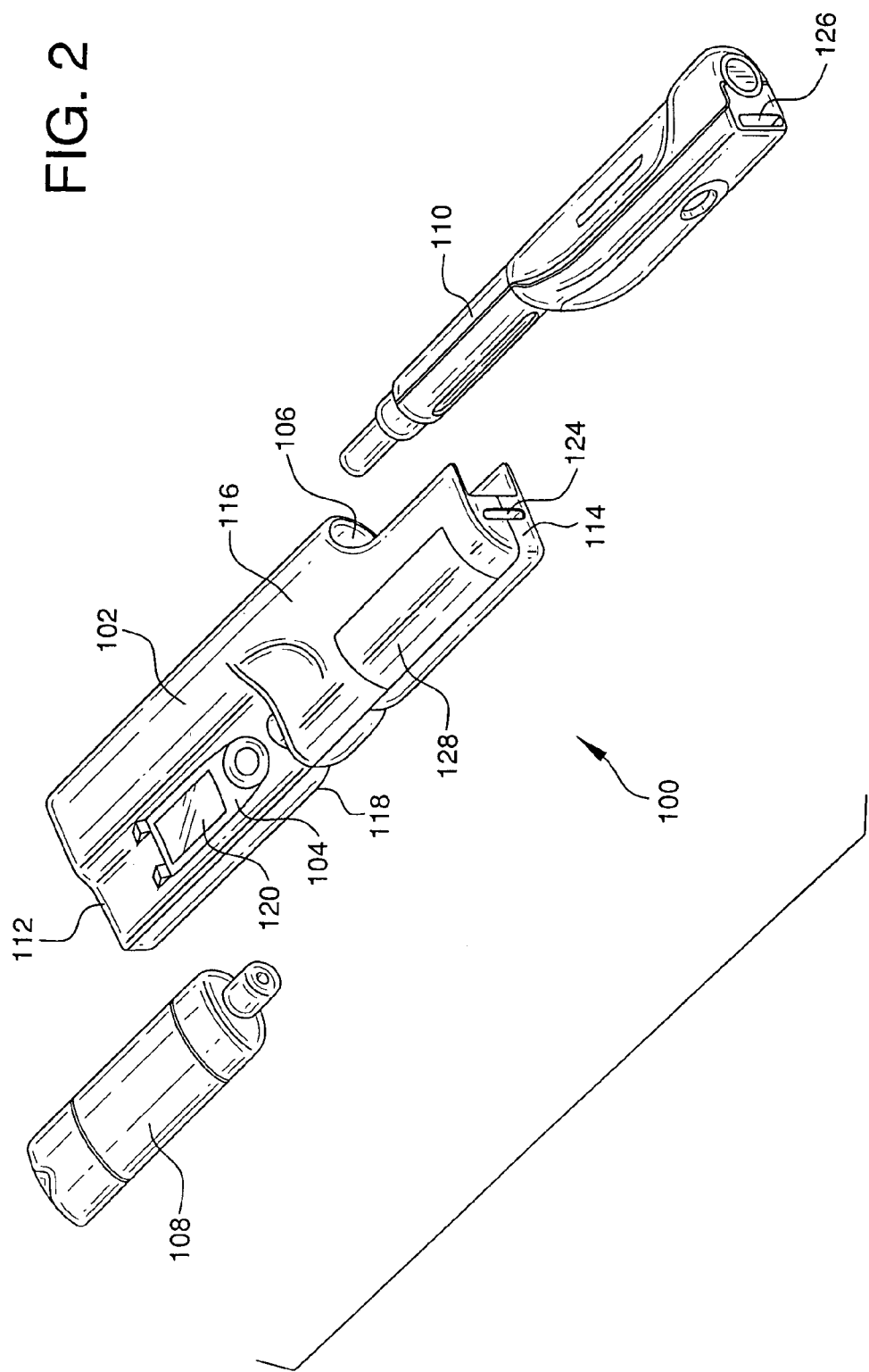
Figure 3:
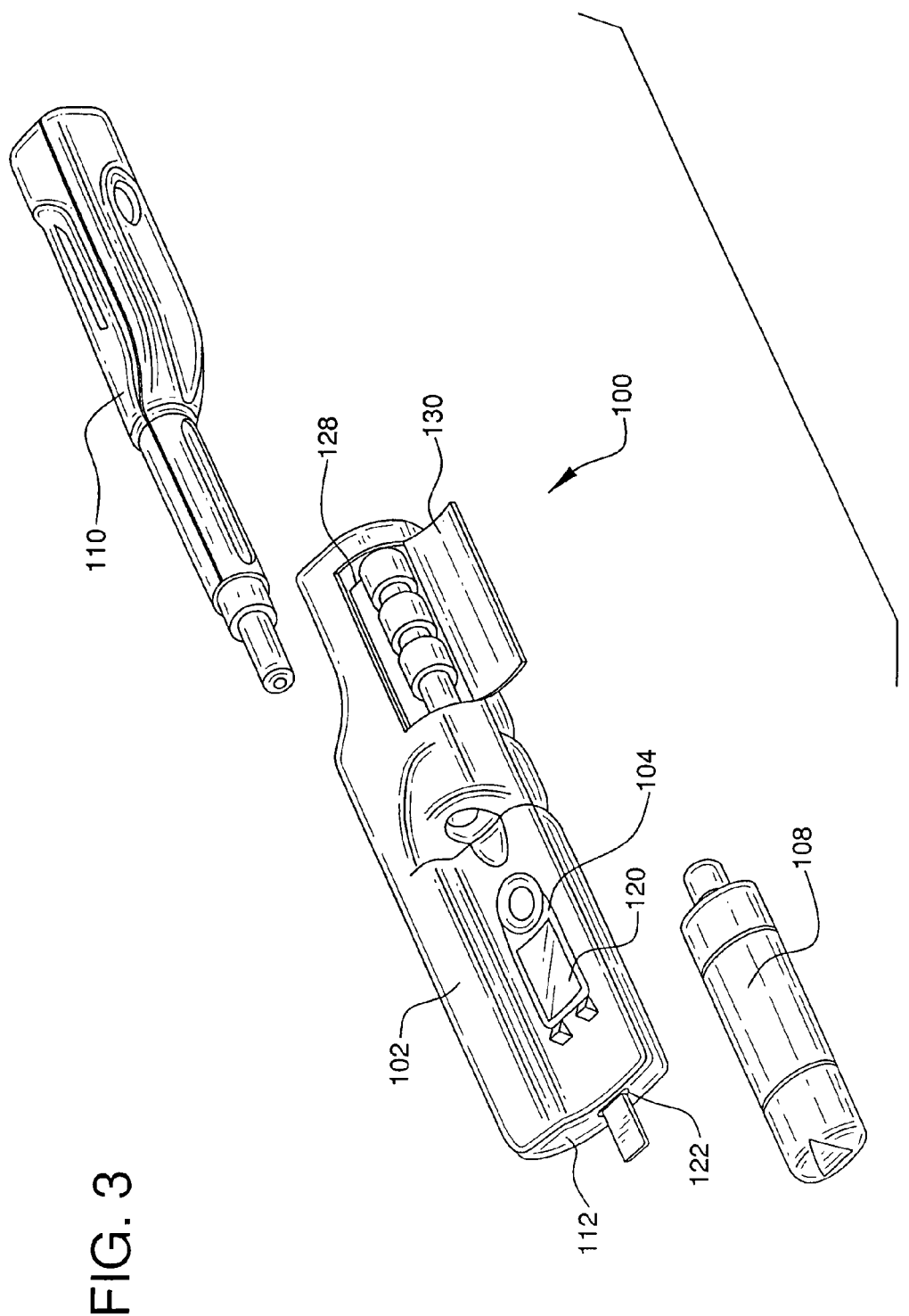

Preferred embodiments of the present invention will now be described with reference to the attached drawing figures. FIGS. 1-3 illustrate an embodiment of a device according to an embodiment of the invention for assisting a patient with diabetes management. A diagnostic and medication delivery system was previously described in U.S. Pat. No. 6,192,891, which is expressly incorporated herein in its entirety. The device will be briefly described in connection with FIGS. 28-30.

The system 100 conveniently integrates a medication delivery pen, blood glucose monitor, and lancet into a single portable unit. The system 100 includes a housing 102 having a length defined by first and second end portions 112 and 114 and a thickness defined by opposing upper and lower surfaces 116 and 118. The housing 102 may have an overall rectangular footprint and the upper and lower surfaces 116 and 118 may be planar or, alternatively, may have either concave or convex curvatures. The curvatures of the upper and lower surfaces 116 and 118 need not match one another. In general, the housing 102 should have a configuration that allows it to be easily grasped and manipulated and thus is not limited to the shape shown in FIG. 1. The housing may be conveniently formed from two shells fastened together to form an enclosure in which the various components discussed below may be located.

The housing 102 provides mounting locations for a medication delivery pen, lancet, and glucose monitoring meter. Specifically, a lancet compartment 104 and pen compartment 106 are integrally formed with and embedded in the housing 102. The lancet compartment 104 is configured to receive a lancet 108 so that the lancet engages and slides in the lancet compartment in a manner that allows it to be easily inserted and removed. Likewise, the pen compartment 106 is configured to receive a medication delivery pen 110. When inserted in their respective compartments, a portion of the body of the lancet and pen are exposed so that they are readily accessible to the user. However, the compartments each include portions that extend internal to the housing 102 in which the lancet of the lancet and the needle of the pen are to be situated. Accordingly, the lancet and needle are protected by the housing 102 from environmental contamination. Thus, housing 102 provides protection to the needle of the pen, eliminating the need for a separate pen cap. Typically when not in use, a conventional lancet is stored with an open port or cover that exposes the lancet to the environment for possible contamination. However, when packaged in housing 102 of the present invention, the lancing port is completely covered providing protection from the environment to the lancet.

The medication delivery pen 110 may be of any type known to those of ordinary skill in the art. In general, the pen has a drive mechanism for accurate dosing and ease of use. A dosage mechanism such as a rotatable knob allows the user to accurately adjust the amount of medication that will be injected by the pen from a prepackaged vial of medication. To inject the dose of medication, the user inserts the needle under the skin and depresses the knob once as far as it will depress.

The pen may be an entirely mechanical device or it may be combined with electronic circuitry to accurately set and/or indicate the dosage of medication that is injected into the user. The electronic circuitry may also serve to record data such as the date, time, amount of medication injected, and so on. The data can be displayed on a display located on the pen. The display may be a mechanical display or an electronic display, depending on whether the pen is a mechanical or electronic pen. The information can also be downloaded via a data port 126 to a computer or other electronic storage device so that it may be subsequently reviewed by the user or a health professional. Data port 126 is preferably an electronic connector, but as will be appreciated by those of skill in the art, an infrared port or any wireless port could be substituted to perform a data exchange function without departing from the present invention. Likewise, data may be uploaded to the pen via data port 126 to install, for example, updated software. Examples of medication delivery pens that may be employed in the present invention are disclosed in U.S. Pat. Nos. 5,536, 249, 5,827,232 and 5,582,598.

Similar to the medication delivery pen 110, the lancet 108 may be of any type known to those of ordinary skill in the art. The lancet 108 will typically include an actuator such as a button for actuating a mechanism that displaces a disposable lancet. The mechanism also returns the lancet to its initial position after it has been inserted into the finger of the user.

A glucose monitor is integrated into housing 102. The glucose monitor includes a display 120, a reaction chamber (not shown) disposed in the housing 102, and a test strip interface 122. The test strip interface 122 is located on the first end 112 of the housing 102 proximate the lancet compartment 104. A disposable test strip on which a blood sample is placed is inserted into the test strip interface 122. When a blood sample enters into the reaction chamber, the blood glucose level is measured using well-known electrochemical or reflectance techniques. In some embodiments of the invention electrochemical techniques are preferred because they require a relatively small sample of blood, employ a small test strip, and provide a quick response.

Electronics such as a microprocessor and other components, e.g., batteries, associated with the glucose monitor are located in the enclosure of housing 102. The electronic circuitry determines and stores the blood glucose level analyzed in the reaction chamber. A bidirectional data port 124 located on the housing 102 is coupled to the electronic circuitry for transferring data to or from an external device such as a computer, phone jack or a communication network. It should be noted that in some embodiments of the invention employing an electronic medication delivery pen having downloading capabilities, data ports 124 and 126 may be combined so that only a single port is required on housing 102. Moreover, aside from the data ports, the electronic pen and glucose monitor also may be in communication with one another both to share data and eliminate redundant components. For example, a single display may be provided on the housing for displaying the data from both the glucose monitor and the electronic pen. Furthermore, some embodiments of the invention may employ a third display that integrates and displays the data from both the electronic pen and the glucose monitor.

In those embodiments of the invention that employ a mechanical delivery pen, the display located on the housing may be configured so that it automatically switches between two modes. In the first mode, when the pen is installed in the compartment 106 the display displays the blood glucose data. When the pen is removed from its compartment, the display switches to a mode that allows information from the medication delivery pen to be manually entered. This allows the patient to use the invention as a simple electronic log book to recall data from memory. Specifically, the user can enter the number of insulin units that are injected so that this data is stored in the electronics associated with the glucose monitor for subsequent downloading. This arrangement eliminates the need for manually recording the insulin dosage, which would otherwise be required with a mechanical pen. After the pen has been reinstalled in its compartment, the display automatically returns to displaying glucose levels.

In the particular embodiment of the invention shown in FIGS. 1-3, the display 120 of the glucose monitor is located in the lancet compartment 104 and forms a portion of the inner surface defining lancet compartment 104. Accordingly, the display 120 is only accessible when the lancet 108 has been removed from the lancet compartment 104 and is therefore protected when the lancet 108 is in place.

The housing 102 may optionally include an accessory compartment 128 for storing such ancillary items as test strips, lancets, and needles. The test strips may be housed in a container that itself is stored in the accessory compartment 128. In contrast to pen and lancet compartments 106 and 104, accessory compartment 128 includes a cover 130 that may be snapped or pivotally mounted to the housing 102. When closed, the cover 130 is flush with the surface of the housing 102. A desiccant may also be provided in accessory compartment 128 to enhance the useful lifetime of the test strips. In some embodiments of the invention the accessory compartment may be partitioned into two or more portions. One portion of the compartment can store unused items while another partition can be used to store used items such as used test strips until they can be otherwise disposed of.

The particular arrangement of components in the housing 102 which is depicted in the embodiment of the invention shown in the drawing figures allows the system to be used in a convenient fashion while reducing the likelihood that any of the components will be used improperly or in an improper sequence. For example, the pen and lancet compartments 106 and 104 are located on opposing ends of the housing to ensure an even distribution of weight along the housing and also to reduce the chance that the user will inadvertently interchange the medication delivery pen 110 and the lancet 108. In addition, the display 120 of the blood glucose monitor is located in the lancet compartment 104 so that it is only exposed when it is needed, e.g., immediately after blood has been drawn by the lancet 108. Likewise, the test strip interface 122 is located on the same end of the housing as the lancet compartment 104 since both will be used when monitoring blood glucose levels. Furthermore, the pen, lancet and accessory compartments 106, 104, and 128 may all be located on the same surface, e.g., upper surface 116, of housing 102. Of course, the present invention is not limited to the arrangement of the components shown in the figures. Rather, the invention contemplates that the components may be arranged in a variety of different configurations. For example, in some embodiments of the invention the pen and lancet compartments may be located on the same end of the housing rather than on opposite ends. Similarly, the display 120 of the glucose monitor need not be located in the lancet compartment but may be placed on any portion of the housing 102.

Figure 4A:
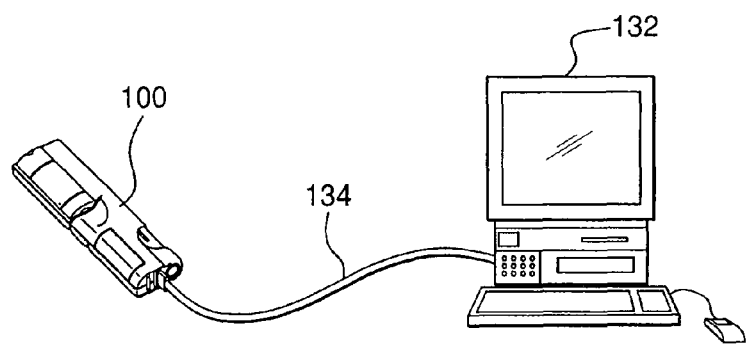
FIGS. 4A-4C illustrate various embodiments of the device of FIGS. 1-3 connected to a computer for data transfer and enhanced analysis.
Figure 4B:
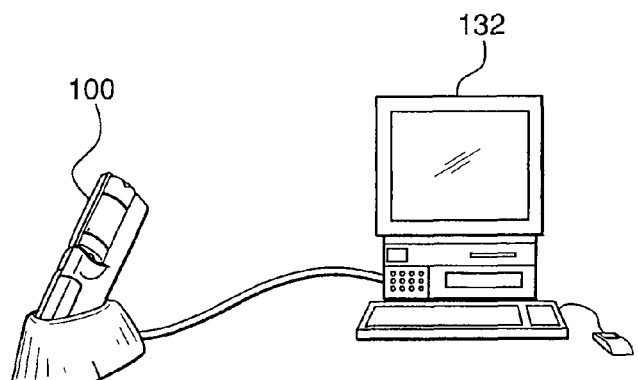
Figure 4C:
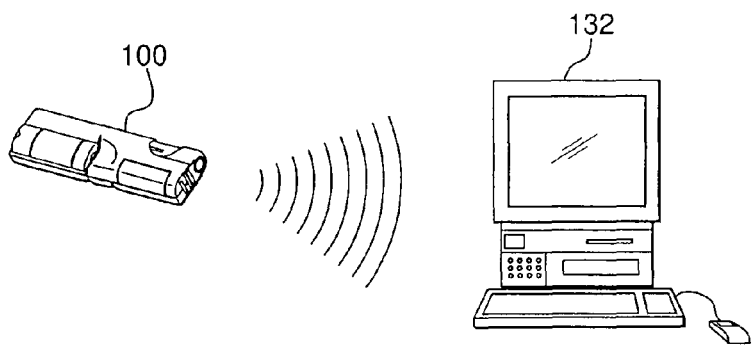

According to an embodiment of the invention, the above described diagnostic and medication delivery system is enhanced to monitor dosage and patient data and notify the patient if they stray from their therapy target. As shown in FIGS. 4A-4C, the device is connected to a computer 132 through data port 124 as described above. In this manner, specific therapy regimen can be programmed into the system at startup, and data from the device can be transferred to a PC 132 over a network for detailed analysis.

FIG. 4A illustrates the device 100 connected to a computer 132 through a cable 134 with a connector adapted to connect to data port 124. FIG. 4B illustrates the device 100 connected to computer 132 through a convenient cradle 136 adapted to accept and support the device 100 while at the same time making an appropriate electrical connection to data port 124. FIG. 4C illustrates a wireless connection between device 100 and computer 132. The wireless connection can be implemented through an infrared transmitter/receiver, or through any other wireless communication method such as, for example, through the Bluetooth or 802.11b protocols.

The diagnostic and medication delivery system 100 is particularly advantageous when used in conjunction with a disease management paradigm. Preferably in connection with a consultation with a health care provider, the device 100 is programmed with specific therapy regimen data. This process is advantageous in that it ensures and guides target setting. Also, health care professional (HCP) and patient partnering is encouraged at this stage.

The device 100 assesses progress verses targets with each SMBG reading, and deviation from targets causes intervention in real time. Further more, the definition of "deviating from target" can be as sophisticated as necessary. The device 100 can alert the user, not only if the target is missed on a particular reading, but also if the historical data stored in the unit indicates failure to progress towards the target, consistent-prandial highs, or the interaction of dose levels and glucose measures, for example.

If an alert is necessary, the patient simply connects the data port 124 to a PC 132 or communication network, as appropriate, to receive more sophisticated analysis, and opportunity for self-assessment of performance related to key factors, and suggestions for actions to take to improve performance. The connection can be made through an appropriately configured cradle for the device, a cable, or an IR or other wireless link.

FIGS. 5-8 illustrate exemplary screen shots of a display for setting up the device 100 according to an embodiment of the present invention, when the device 100 is connected to a PC 132 or a network. FIG. 7 illustrates a data entry screen shot. As shown, the screen includes patient name, current regimen, glucose control data, and standards of care data.

Figure 9:
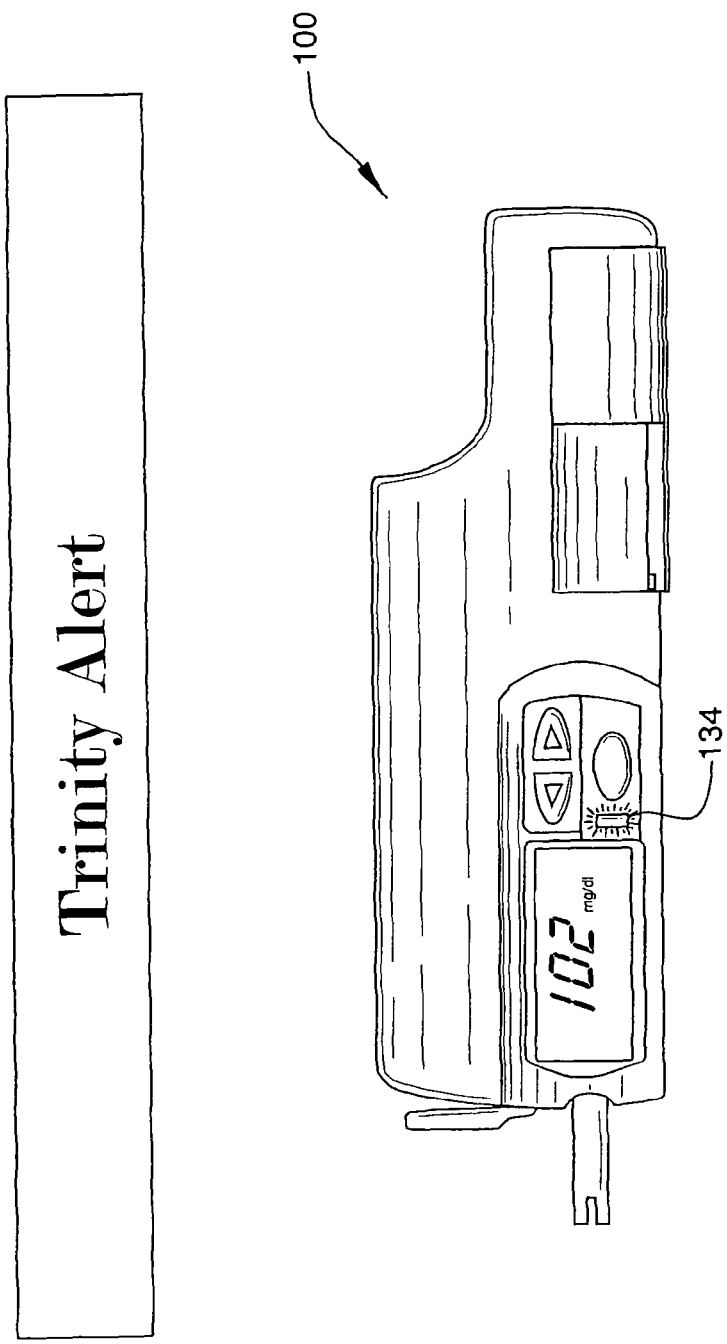
FIG. 9 illustrates an alert generated by a device in accordance with an embodiment of the invention.

In use, the device 100 alerts the user when doses are due, when SMBG readings need to be taken, and if the SMBG levels are outside of target. If the user receives an alert, they reconnect the device to a PC 132 or network for further analysis and determination of appropriate corrective action. FIG. 9 illustrates a device 100 displaying an alert after a SMBG reading. Upon completion of a SMBG test, the device alerts the user if the glucose value reported indicates a departure from their path to targeted control. Once an alert is received, the user would download the device data to a PC for analysis, information and action suggestions.

Figure 10:
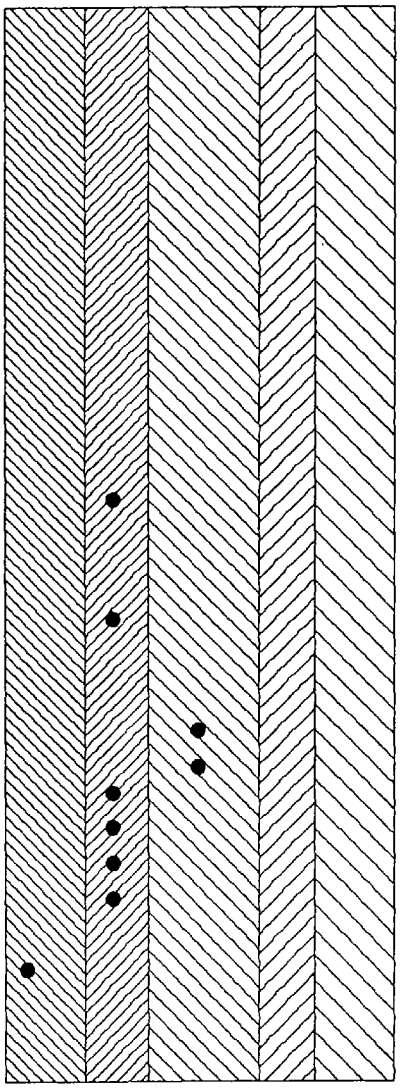
FIG. 10 illustrates is a screen shot of a display generated by a system upon receiving data from a medication delivery and property measurement device.

Preferred embodiments of the present invention advantageously provide an opportunity for the patient to perform self-assessment in order to receive highly relevant suggestions for improvement of their disease management. An exemplary screen shot of a graphical illustration of recent readings generated from data transferred from the device 100 to the PC 132 or network is shown in FIG. 10. In the example illustrated in FIG. 10, an alert was generated because more than 50% of the patient's SMBG readings were outside of their target, or the "green zone."

FIGS. 11-15 illustrate a novel self-assessment system and method according to an embodiment of the present invention.

Figure 11:
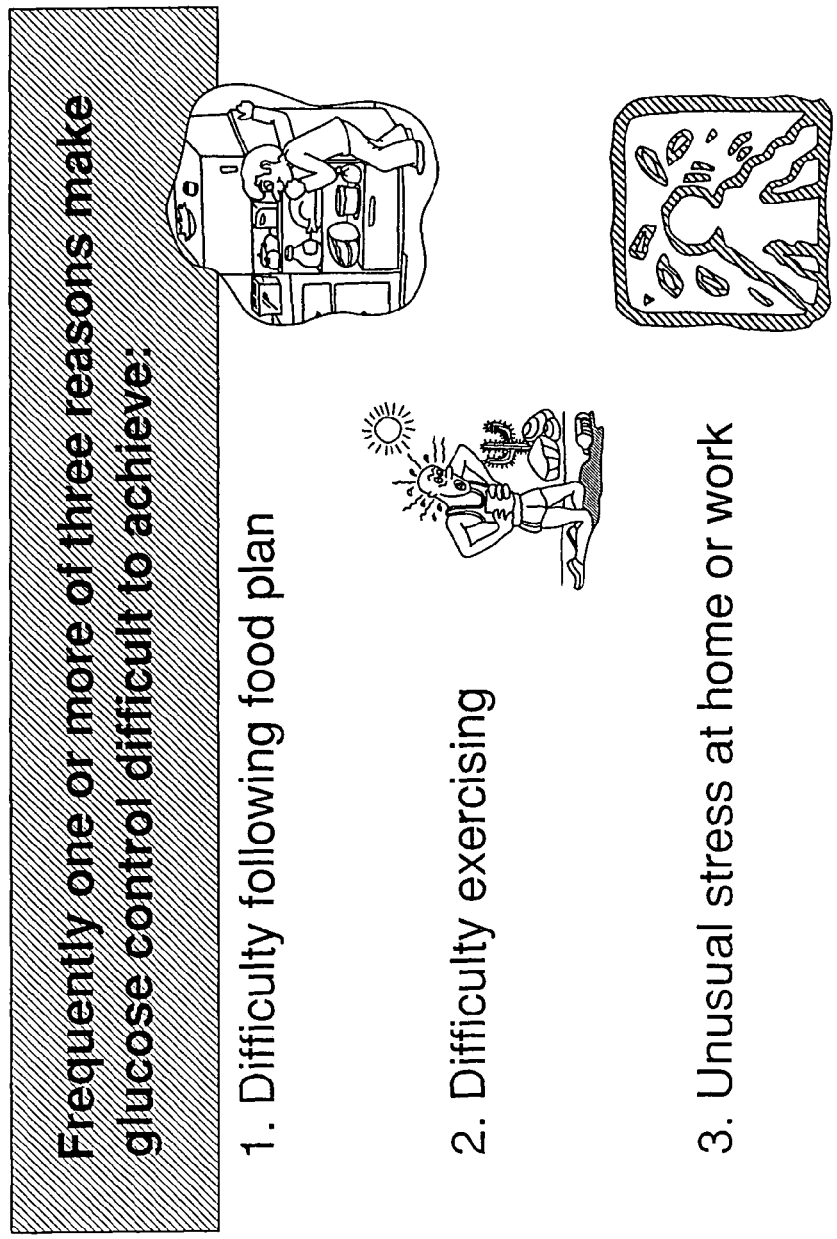
Figure 12:
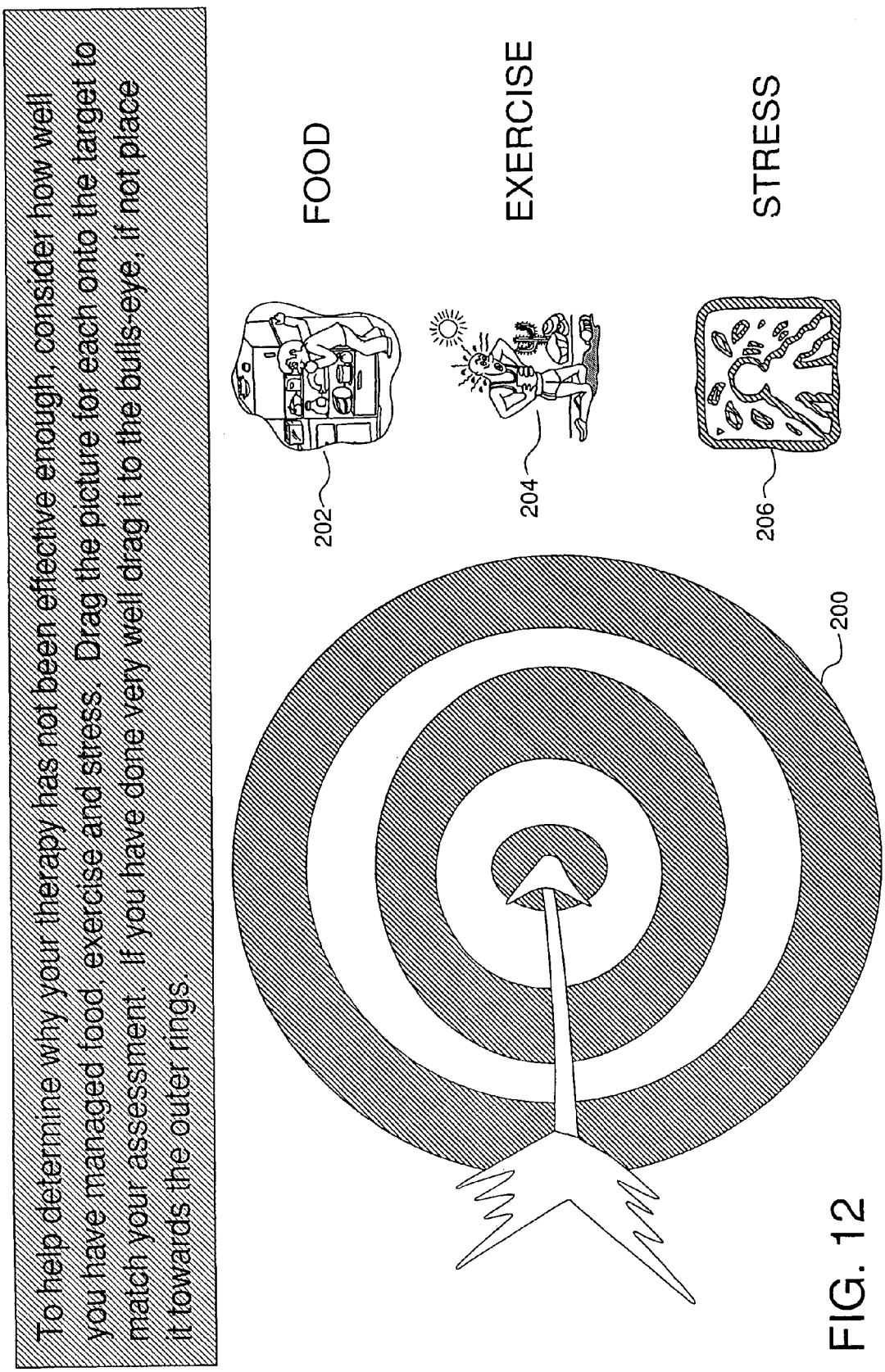
Figure 13:
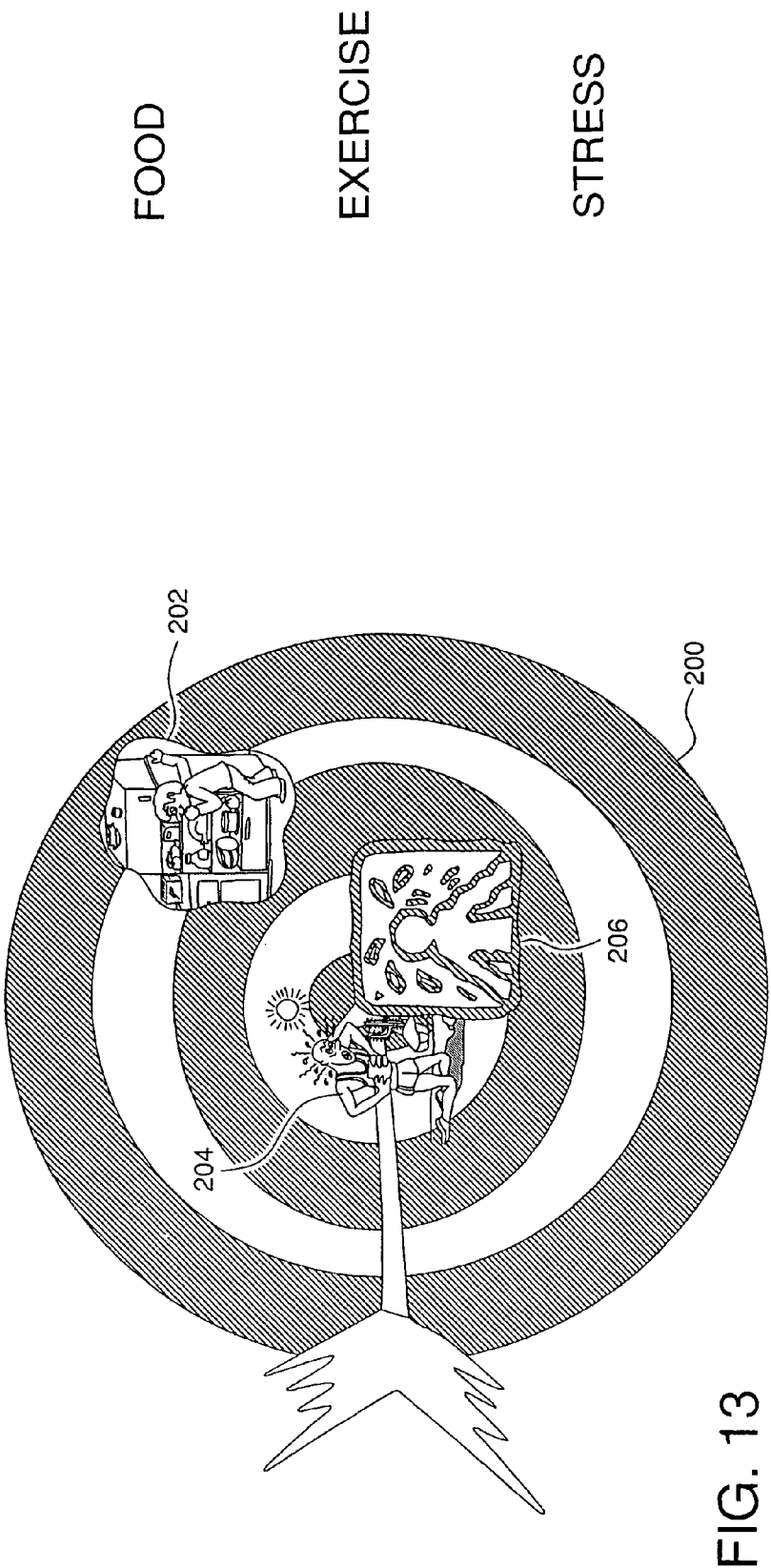

FIG. 11 illustrates an informational screen shot informing the patient of three common factors which are known to cause difficulty in glucose control. FIG. 12 illustrates a graphical user interface that enables the patient to self-assess their performance in several key areas. A large target image 200 is presented, along with several factor icons 202, 204, 206. The patient moves or "drags" the icons 202, 204, 206 onto a position on the target image 200 representative of their self-assessment of their performance relative to that factor. A target image 200 having icons 202, 204, 206 dragged onto it by a patient is illustrated in FIG. 13.

FIG. 14 illustrates a follow-up screen generated upon analysis of the patient's self-assessment. In the exemplary instance, food plan was indicated as a trouble area. Thus, the system provides follow up questions to determine the best course of action. FIG. 15 illustrates the choices selected as answers to each questions by a patient.

Finally, utilizing the data received from the patient, the device 100, and a set of guidelines, such as SDM guidelines, actionable alternatives are presented to the patient. The actionable alternatives could include, for example, the opportunity to review nutrition education material, daily nutrition tracking tools, hyperlinks to nutrition counseling resources, testimonials from successful people who overcame similar circumstances, links to support groups, support chat rooms, a link to a participating RPh, recommended reading, language to facilitate discussion of the patient's problem with their HCP, and additional self-assessment tools to identify the dynamics of their negative eating habits (such as, for example, time of day or circumstance drivers).

The present invention advantageously takes advantage of the knowledge and experience gained through the use of successful guidelines, such as SDM guidelines, and combines them with instant feedback and actionable alternatives and recommendations.

Of course, the principles of the present invention could be embodied in many varying forms. As an example, the above described combination of a device 100 with the system could be modified to eliminate the device, and depend on patient manually entering data, nurse or HCP entering of data, or any other combination. Furthermore, as will be readily understood, the principles of the invention are applicable far beyond diabetes management, although diabetes management is contemplated as the exemplary and preferred embodiment. Many varying medical uses, and non-medical uses, are contemplated. The principles of the invention are useful in any diagnostic and feedback system, in which guidelines are used to determine future courses of action.

While the invention herein disclosed has been described by means of specific embodiments and applications thereof, numerous modifications and variations could be made thereto by those skilled in the art without departing from the scope of the invention set forth in the claims.

What is claimed is:

1. A device for assessment and corrective action based on guidelines comprising:
   a graphical user interface including a target image and at least one factor icon representing a factor relevant to glucose control that a user moves to a position on said target image, said position being representative of the user's self assessment of user performance relative to said factor, said user performance ranging from good to poor;
   a memory adapted to store self-assessment values based on said position on said target image and a plurality of actionable alternatives that are presentable to the user;
   a processor adapted to select a subset among said plurality of actionable alternatives stored in said memory based on said stored self assessment values; and
   a display adapted to display said subset of suggestion data.

2. The device of claim 1, wherein the at least one factor icon is representative of at least one among the set including diet, exercise and stress.

3. The device of claim 1, wherein good performance is determined by placement of the factor icon at or near the target center, and poor performance is determined by placement of the factor icon at or near the target edge.

4. A method of assessment and corrective action based on guidelines comprising the steps of:
   in a graphical user interface comprising a target image and at least one factor icon representing a factor relevant to glucose control, moving said factor icon to a position on said target image, said position being representative of a user's self assessment of user performance related to said factor, said user performance ranging from good to poor; and
   based on said position, selecting a subset from a plurality of actionable alternatives and displaying said selected subset of actionable alternatives on a display.

5. The method of claim 4, wherein the at least one factor icon is representative of at least one among the set including diet, exercise and stress.

6. The method of claim 4, wherein good performance is determined by placement of the factor icon at or near the target center, and poor performance is determined by placement of the factor icon at or near the target edge.

7. A computer readable medium of instructions adapted to control a system for assessment of disease management comprising:
   a first set of instruction adapted to control a graphical user interface to display a target image and at least one factor icon;
   a second set of instructions adapted to control the system to allow a user to move the at least one factor icon representing a factor relevant to glucose control to a position on said target image, said position being representative of the user's self assessment of user performance relative to said factor, said user performance ranging from good to poor;
   a third set of instructions adapted to select, based on said self-assessment, a subset from a plurality of actionable alternatives for performance improvement; and
   a fourth set of instructions adapted to display said selected subset among said plurality of actionable alternatives.

8. The computer readable medium of instructions of claim 7, wherein said suggestions include links to instructional materials.

9. The computer readable medium of instructions of claim 7, wherein said suggestions comprise instructional audio-visual presentations.

10. The computer readable medium of instructions of claim 7, wherein the at least one factor icon is representative of at least one among the set including diet, exercise and stress.

11. The computer readable medium of instructions of claim 7, wherein good performance is determined by placement of the factor icon at or near the target center, and poor performance is determined by placement of the factor icon at or near the target edge.

* * * * *